(12) United States Patent
Hustveit

(10) Patent No.: US 8,276,586 B2
(45) Date of Patent: Oct. 2, 2012

(54) VALVE FOR A BREATHING APPARATUS

(76) Inventor: Olav Hustveit, Oslo (NO)

(*) Notice: Subject to any disclaimer, the term of this patent is extended or adjusted under 35 U.S.C. 154(b) by 1130 days.

(21) Appl. No.: 12/158,792

(22) PCT Filed: Dec. 28, 2006

(86) PCT No.: PCT/NO2006/000501
§ 371 (c)(1),
(2), (4) Date: Jun. 23, 2008

(87) PCT Pub. No.: WO2007/075090
PCT Pub. Date: Jul. 5, 2007

(65) Prior Publication Data
US 2009/0007917 A1 Jan. 8, 2009

(30) Foreign Application Priority Data
Dec. 29, 2005 (GB) .................................. 0526571.5

(51) Int. Cl.
*A62B 9/02* (2006.01)
*A62B 9/00* (2006.01)
(52) U.S. Cl. .............................. 128/205.24; 128/207.16
(58) Field of Classification Search ............. 128/205.24, 128/205.13, 203.11, 207.12, 207.16; 137/15.17–15.26, 855, 102, 495, 908
See application file for complete search history.

(56) References Cited

U.S. PATENT DOCUMENTS

| | | | |
|---|---|---|---|
| 4,192,301 A | 3/1980 | Hardwick | |
| 4,453,543 A * | 6/1984 | Kohnke et al. | 128/203.28 |
| 5,146,914 A * | 9/1992 | Sturrock | 128/203.11 |
| 5,438,981 A * | 8/1995 | Starr et al. | 128/205.24 |
| 5,803,074 A * | 9/1998 | Pope | 128/205.24 |
| 6,585,000 B2 * | 7/2003 | Radford | 137/527 |
| 6,923,181 B2 * | 8/2005 | Tuck | 128/205.24 |
| 2010/0170509 A1 * | 7/2010 | Moody et al. | 128/203.12 |
| 2010/0329911 A1 * | 12/2010 | Borst et al. | 417/559 |

FOREIGN PATENT DOCUMENTS

| | | |
|---|---|---|
| EP | 0 710 488 A1 | 5/1996 |
| EP | 1 382 364 A1 | 1/2004 |
| GB | 2 406 285 A | 3/2005 |
| WO | WO 98/23318 | 6/1998 |
| WO | WO 01/76673 A1 | 10/2001 |
| WO | WO 02051486 A1 | 7/2002 |

* cited by examiner

*Primary Examiner* — Allana Lewin
(74) *Attorney, Agent, or Firm* — Knobbe, Martens, Olson & Bear LLP

(57) ABSTRACT

A respiratory valve, comprising a valve housing with a chamber, inlet (21) and respiration (22) openings. The chamber is limited by an arcuated or aslant interior wall section (18) extending from a lower part and into an upper part of the chamber, and is terminated in the upper part of the chamber, under the respiration opening. An outlet opening (23) is provided in the interior wall section. An elongated valve flap (32) in the form of a resilient plate element fixed to the lower part of the chamber terminates in the upper part of chamber. The flap is wide enough to cover the outlet opening, and is adapted to be positioned, in a rest position, in a distance from the interior wall section, and, in a work position, in contact with a part of the interior wall section. In the work position, the flap substantially covers and closes the outlet opening, and establishes a passageway between the inlet and respiration openings.

10 Claims, 11 Drawing Sheets

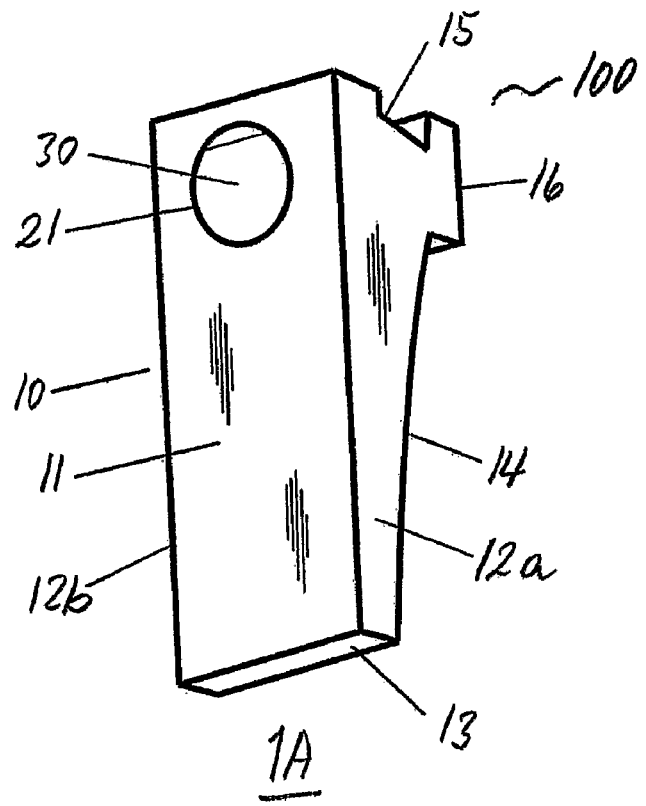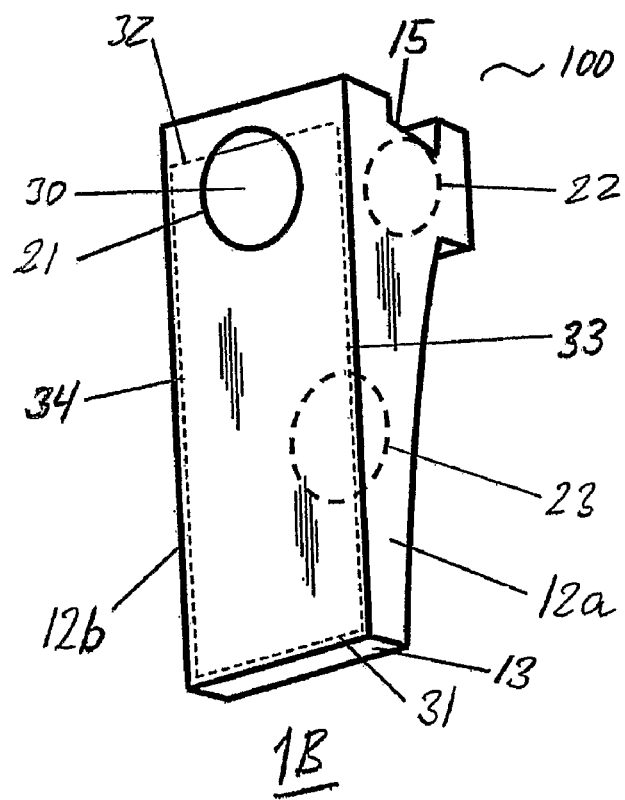

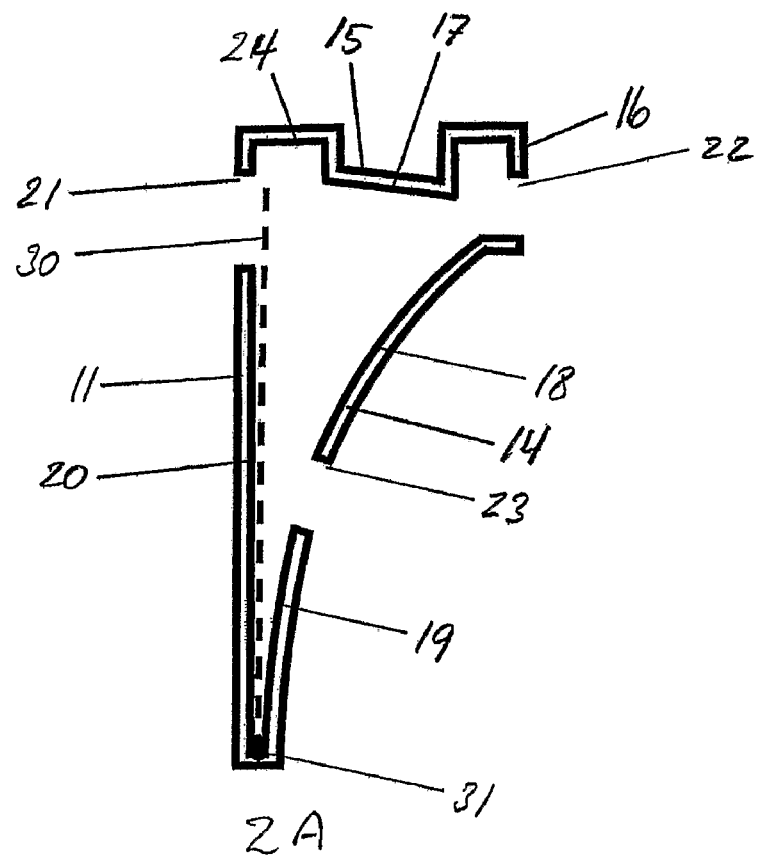
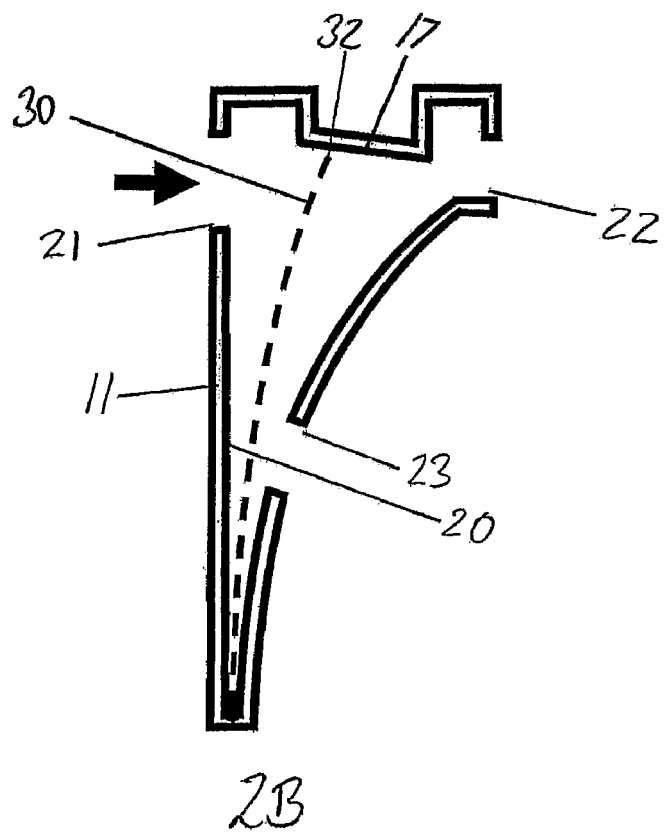

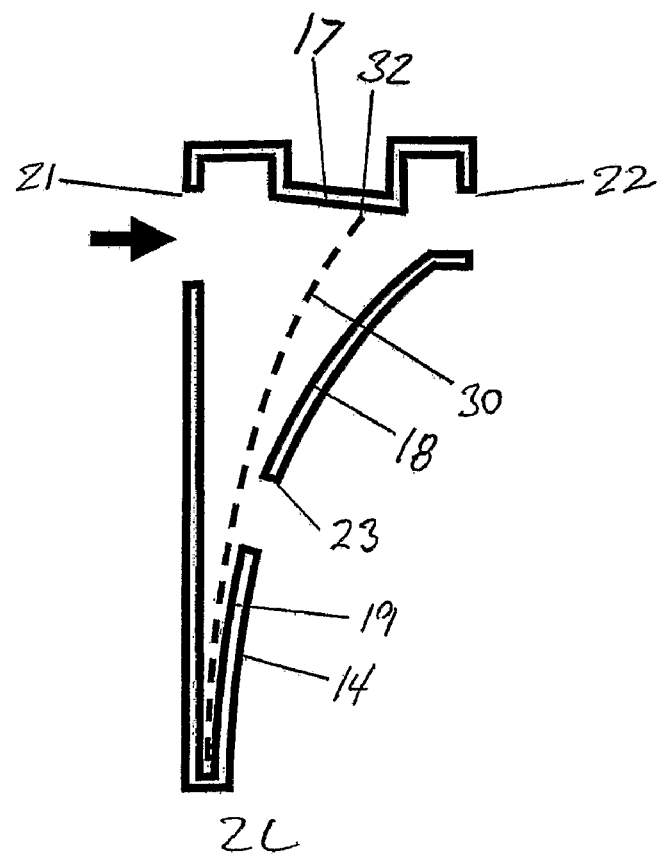
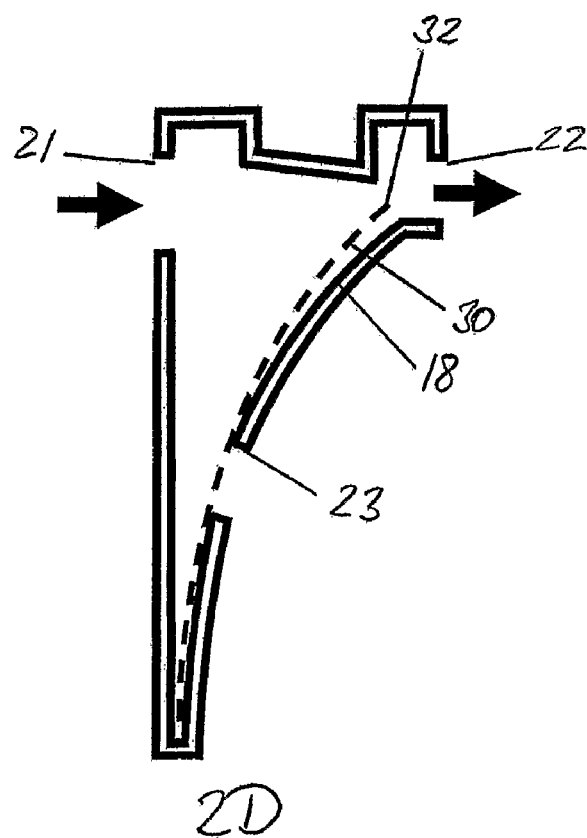

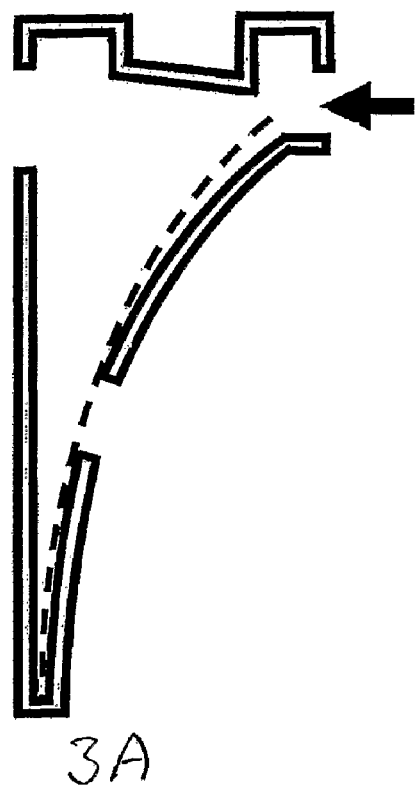
3A
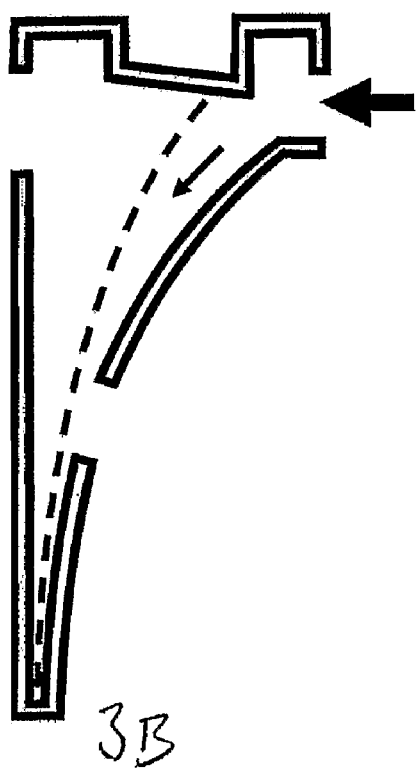
3B

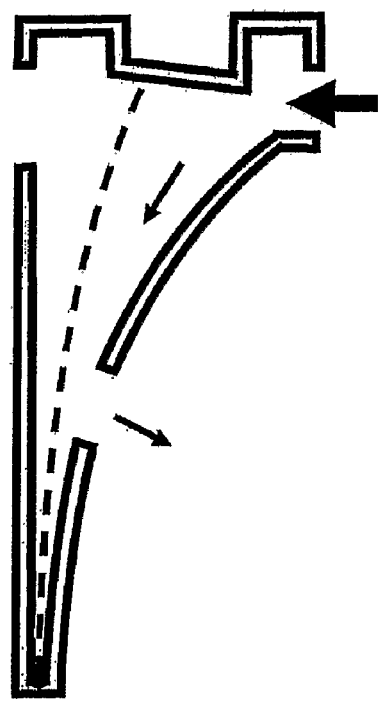
3C
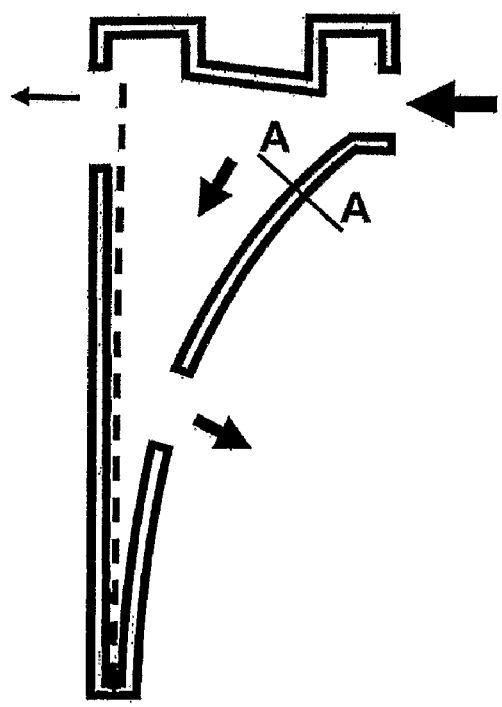
3D

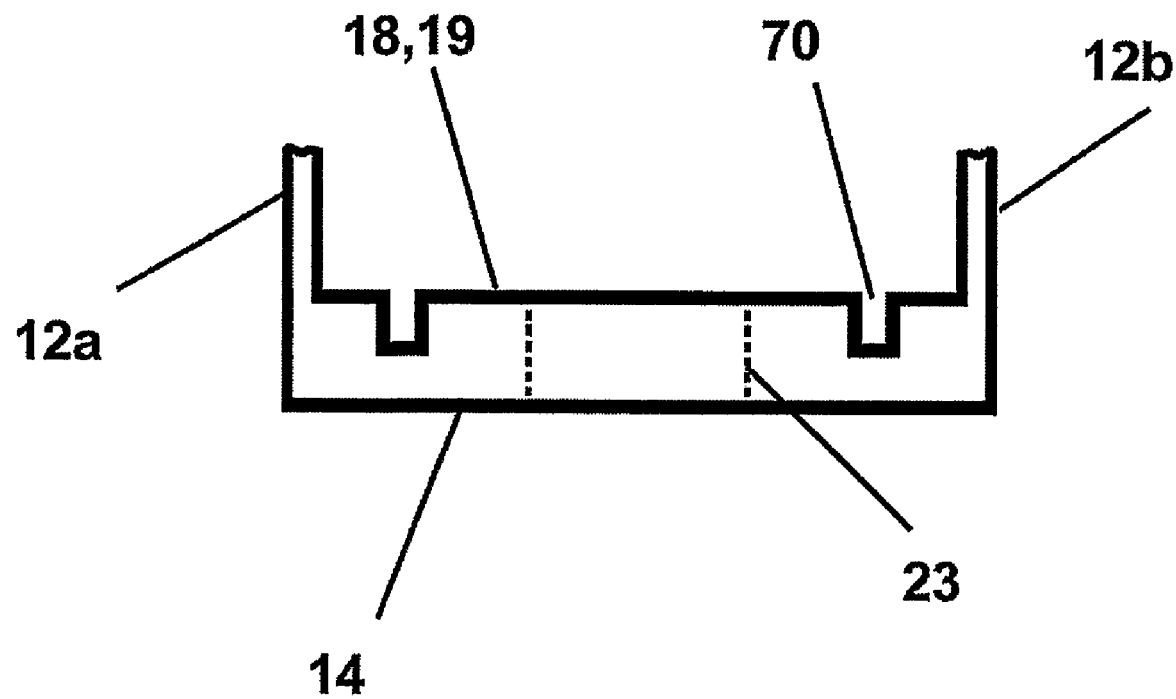
3E

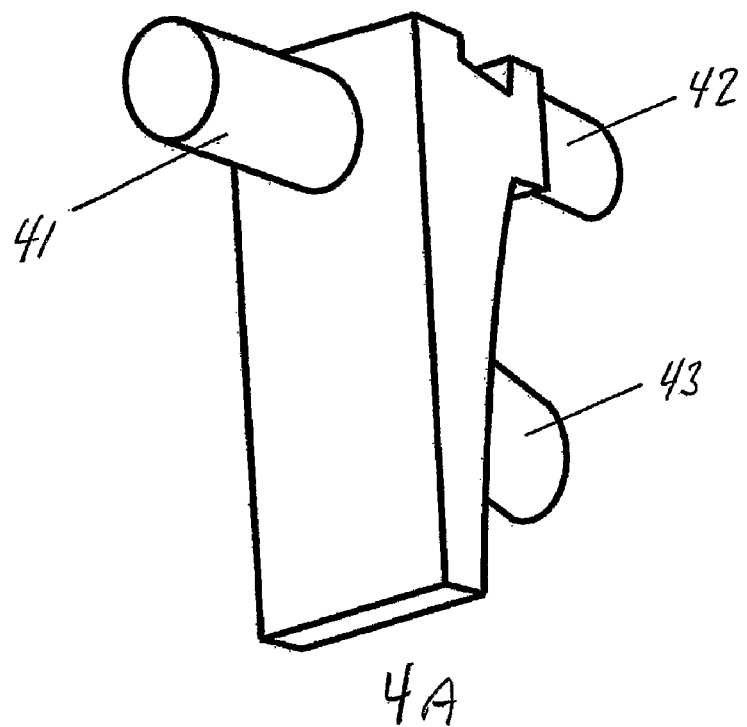
4A
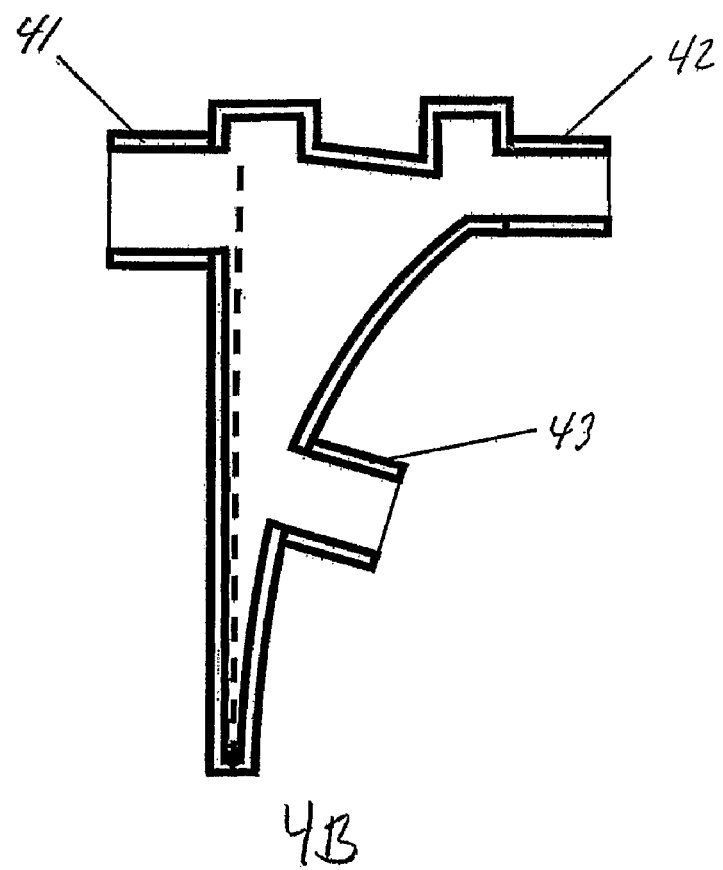
4B

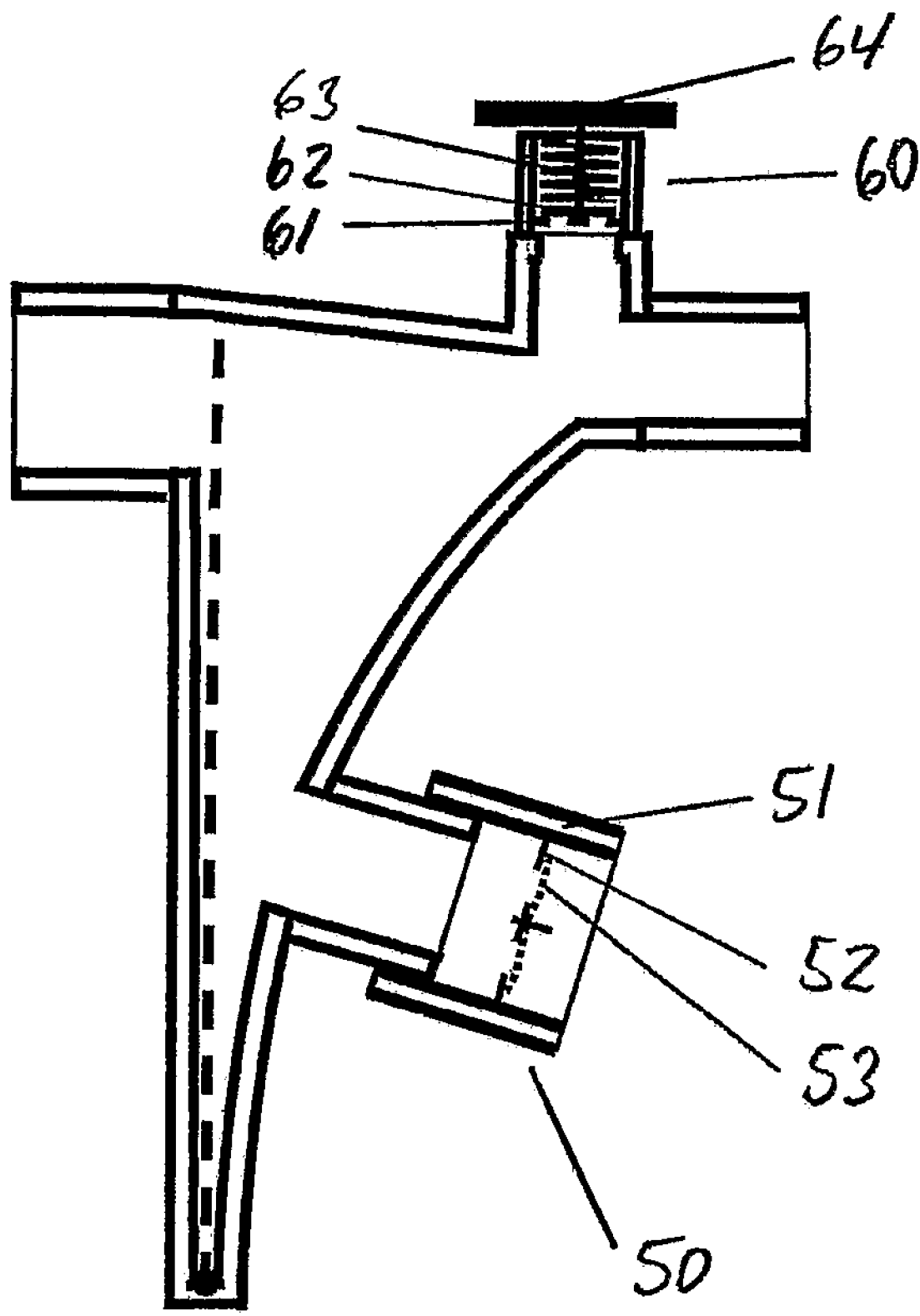

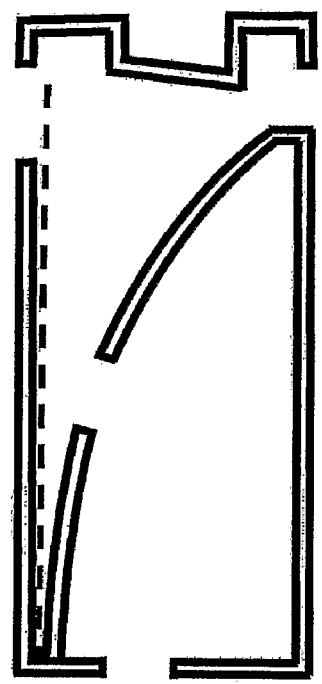
6A
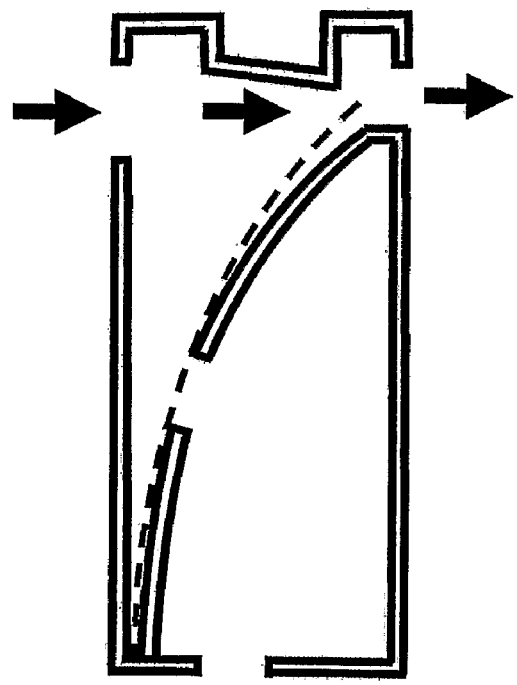
6B

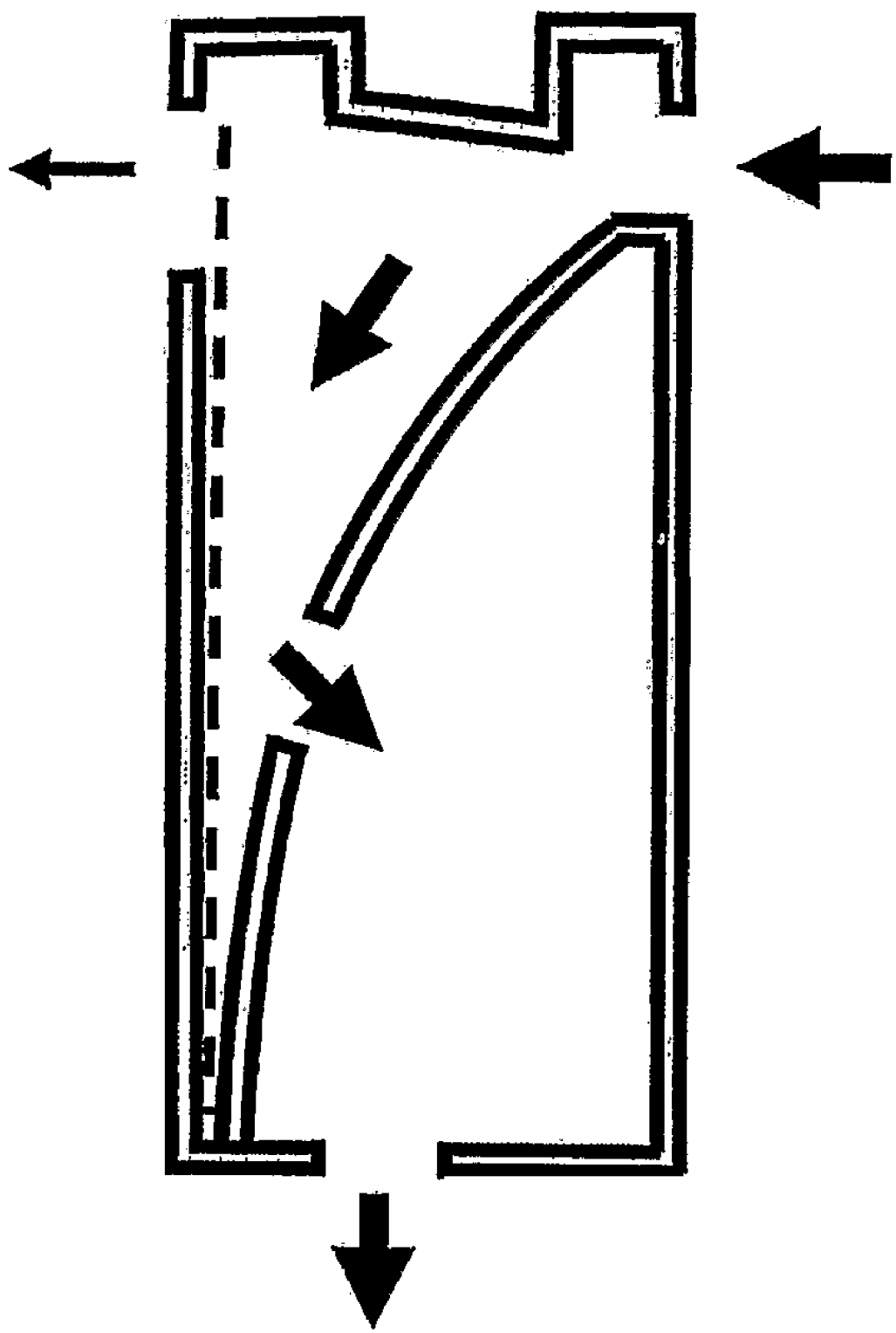
6C

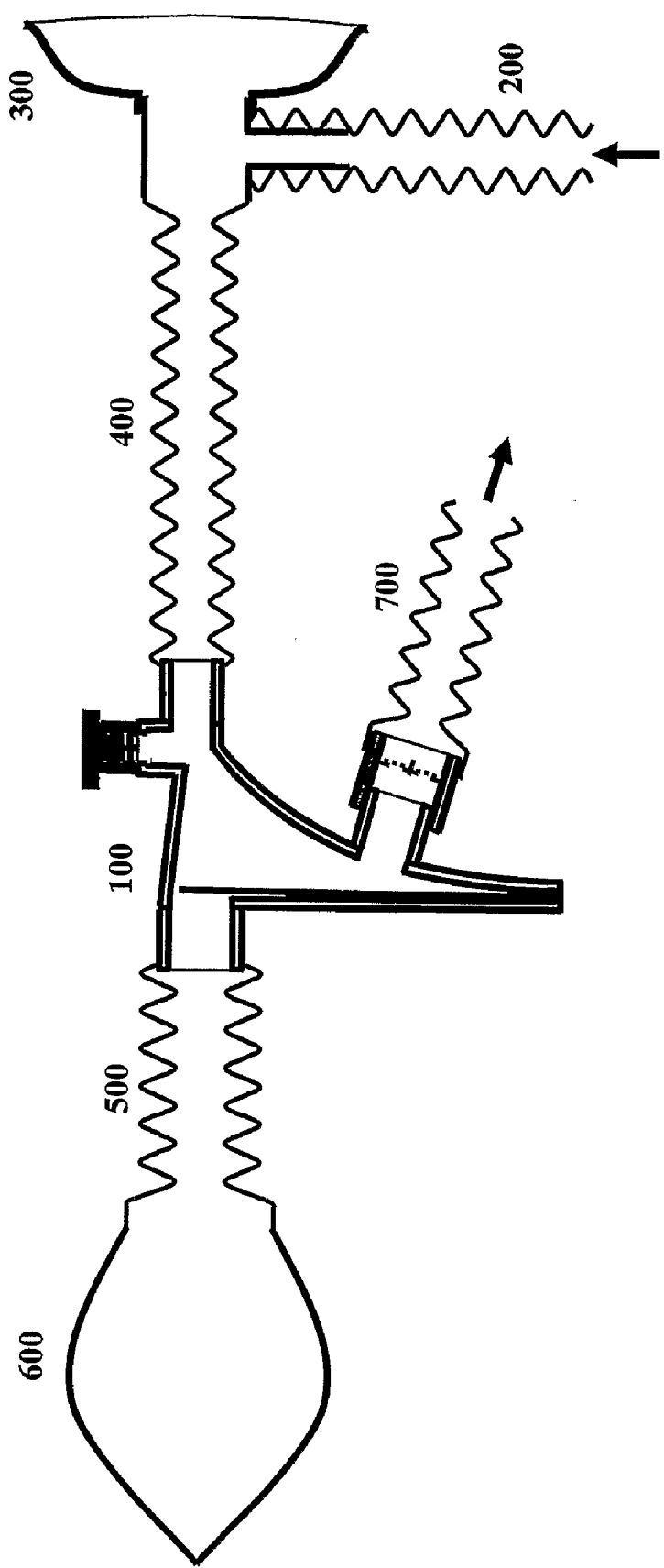

VALVE FOR A BREATHING APPARATUS

CROSS REFERENCE TO RELATED APPLICATIONS

This application claims the benefit and priority to and is a U.S. National Phase of PCT International Application Number PCT/NO2006/000501, filed on Dec. 28, 2006, which claims priority to United Kingdom Patent Application No. GB 0526571.5, filed on Dec. 29, 2005. The disclosures of the above-referenced application is hereby expressly incorporated by reference in its entirety.

The present invention relates to a valve for a breathing apparatus, and more particularly to a flap-valve that is particularly suitable for use as part of an anaesthesia-breathing apparatus for supplying gas to patient for artificial respiration, supported respiration, anaesthesia purposes or combinations of such purposes.

A valve is commonly used in an anaesthesia-breathing apparatus for performing controlled ventilation or supported ventilation. Typically, the valve is designed to ensure that breathing gas is provided to the patient to maintain proper ventilation, by directing a quantity of fresh breathing gas to the lungs of the patient, and a quantity of exhaled "used" gas to an outlet. When an anaesthetic gas is employed, it is important that the valve operates safely under all conditions, for the safety of the patient as well as the safety of personnel that should not be exposed to the anaesthetic gas. A transition is made between spontaneous respiration and controlled ventilation. A bag is used for assisting the respiration. In a typical anaesthesia-breathing apparatus, the valve fully or partly separates gas exhaled from the patient from gas to be inhaled by the patient. An anaesthesia-breathing apparatus is known from U.S. Pat. No. 4,453,543, which incorporates a comparatively large control valve having multiple ports, and a supplementary valve for allowing a partial re-flow of exhaled or surplus gas into the bag. The control valve includes a reciprocating plunger that is allowed to move between two oppositely located valve seats for separating gas to be inhaled from gas exhaled from the patient.

Another valve is known as the Laerdal-valve, which employs a single, slotted membrane movable in a valve housing for separating gas exhaled from the patient from gas to be provided for inhalation by the patient. The Laerdal-valve is suitable for resuscitation, by requiring a relatively high pressure for gas to the patient to pass the valve.

The AMBU valve, also known as the Ruben's valve, is suitable for assisted ventilation of a patient, as well as for supplying gas for spontaneous breathing. The AMBU valve employs one or two valve flaps made from rubber or a similar material, and requires frequent inspection and flap replacement to ensure safe operation.

Other valves for a breathing apparatus are known from U.S. Pat. No. 4,453,543, WO 01/76673 A1, EP 1 382 364 A1, U.S. Pat. No. 4,192,301, EP 0 710 488 A1, WO 98/23318, and GB 2 406 285 A.

Another valve is known as the Berner valve. The Berner valve is designed for volume controlled as well as pressure controlled ventilation, and has an outlet that allows guiding of the gas discharged from the patient away from the operation theatre environment. The Berner valve employs a spring loaded disc which is allowed to move between two valve seats, and is provided with a second loading spring for selecting an operational mode between volume controlled and pressure controlled ventilation of the patient. The Berner valve requires a rather complicated procedure for its calibration, and comprises a number of mechanical components that need proper care and careful assembly for correct operation of the valve.

When used for pressure controlled ventilation, the valve is set to allow the pressure in the gas being delivered to the patient to reach only a preset pressure level, generally regardless of gas volume being transported through the system. Gas at a pressure level that exceeds the preset pressure level is allowed to escape from the breathing apparatus. An advantage of operating in a pressure controlled ventilation mode during assisted ventilation, with the preset pressure level set to a level at or below what is considered safe, is clearly that the breathing organs of the patient may not be subjected to a pressure that may cause harm or injury. A disadvantage of operating in a pressure controlled ventilation mode is that an operator must at all times carefully observe chest movements of a patient to ensure that breathing gas actually flows into the patient, rather than escaping due to having reached the preset pressure level e.g. as a consequence of a blockage in the respiratory passage.

In volume controlled ventilation, the valve is set to allow any volume, as provided by the operations made by an operator, to be delivered to the patient, generally regardless of pressure. An advantage of operating in a volume controlled ventilation mode during assisted ventilation is that an operator is given full control over the volume of breathing gas being delivered to the patient. A disadvantage of operating in a volume controlled ventilation mode is that an operator must at all times carefully observe the pressure of the breathing gas being delivered to the patient such that the breathing organs of the patient are not subjected to a pressure that may cause harm or injury. Excessive pressure can be avoided by the employment of an additional pressure relief valve, sometimes referred to as a "pop off" valve. The employment of an additional pressure relief valve, however, may neutralize the advantage of volume controlled ventilation.

The Berner valve is provided with a means for manually selecting the operational mode of the valve. Accordingly, when the operator experiences a change in conditions of a patient being supplied with breathing gas in a system employing the Berner valve, such as a transition from a state where the patient returns from assisted breathing to normal breathing, the latter condition often referred to as spontaneous breathing, the operator must manually manipulate the valve control means to change the operational mode from the assisted breathing mode to spontaneous breathing mode. As an example, in a "volume controlled" mode during assisted ventilation, that is, when the patient is incapable of sustaining normal breathing, the operator must continuously be aware of the filling degree of the bag, as the valve may enter a dangerous "deadlock" state if the bag fills up completely. Typically, the only ways to exit from such a dangerous "deadlock" state is to disconnect the gas conduits of the patient system or to manipulate the control means for bringing the valve to the spontaneous breathing mode. The need for manually altering the operational mode of the valve, and the ever present risk of entering a state of potential emergency, requires the presence of a highly skilled, attentive and alert operator. Thus, being dependent on the human element, it may be considered a risk factor that needs to be reduced, preferably eliminated from the operating theatre setting.

Another problem that has been experienced with known valve solutions is the tendency to jam, stick or lock under different circumstances. Jamming, sticking or locking is in part a result of the complex arrangements of known valves, often involving a number of moving parts, the use of tight mechanical tolerances and/or mode control arrangements.

Avoidance of jamming, sticking and locking of prior art valves has up to now required frequent inspections and preventive maintenance operations, which in turn increases wear and further increases the risk of malfunctioning at a critical time.

A further problem addressed by the present invention is the tendency of prior art valves to restrict, or even block, the normal flow of gas as a result of a transition into an undesirable lock-up state in a situation where the exhalation from the patient makes an abrupt change. A typical example of a situation in which such an abrupt change occurs is the rapid increase in the flow or pressure caused by the often occurring event of the patient coughing while being supplied breathing gas through the valve. The incapability of certain types of valves to properly handle rapid changes in pressure or flow can fully or in part be attributed their basic design. Some designs, however, are capable of handling such situations only after careful adjustment, which typically requires use of properly calibrated test gear.

Accordingly, there is a need for a valve that operates safely under a wide range of operating conditions. There is also a need for a valve that does not require demanding routine adjustments and subsequent routine verification of operation in order to ensure safe operation under various operating conditions.

The present invention provides a valve that addresses the above and other problems known for prior art valves.

The present invention provides a valve for a breathing apparatus, comprising the features recited in the accompanying patent claim 1.

Further advantageous features of the valve of the present invention are recited in the accompanying dependent patent claims 2-10.

According to a first aspect of a respiratory valve according to the invention it comprises a valve housing with a chamber, the chamber having an inlet opening and a respiration opening arranged on respective inlet and respiration sides of said chamber, wherein the chamber is limited by an arcuated or aslant interior wall section extending from a lower part of said chamber and into an upper part of said chamber, which interior wall section is terminated in said upper part of said chamber and under the respiration opening, and that the respiratory valve further comprises an outlet opening, said outlet opening having an outlet opening width, said outlet opening being arranged in said interior wall section, and an elongated and in a direction of depth of said housing pliable or movable valve flap in the form of a plate element having a lower part connected to said lower part of said chamber, under the outlet opening, which plate element at the outlet opening is sufficiently wide to cover the outlet opening, and being terminated in an upper part of said interior chamber, which plate element is adapted to be positioned, in a rest position, in a distance from said interior wall section, and, in a work position, proximal to a part of said interior wall section, for in the work position substantially to cover and close the outlet opening and to establish a passageway between the respiration opening and inlet opening.

According to a further aspect of a respiratory valve according to the invention, said inlet opening and said respiration opening are arranged on respective, relative to the valve flap oppositely situated, inlet and respiration sides of said housing.

According to yet a further aspect of a respiratory valve according to the invention, the plate element is adapted to be resilient or is provided with a return spring arrangement for positioning the plate element in the rest position.

According to yet a further aspect of a respiratory valve according to the invention, the valve housing comprises a top wall or a side wall having a part constituting a projection into the upper part of said interior space, which projection does not constitute an obstacle for a movement of the plate element, and which projection extends in a direction of depth of said housing from proximal to the inlet side wall and to a distance from the inlet side wall, said extending approximately corresponding to a distance between said inlet side wall and a point of said termination of said interior wall section in the upper part of said chamber.

According to yet a further aspect of a respiratory valve according to the invention, it comprises at least one of an inlet conduit arranged at the inlet opening, a respiration conduit arranged at the respiration opening and an outlet conduit arranged at the outlet opening.

According to yet a further aspect of a respiratory valve according to the invention, it comprises a PEEP valve arranged in communication with the outlet opening.

According to yet a further aspect of a respiratory valve according to the invention, said outlet opening is arranged in a central or lower part of said interior wall section.

According to yet a further aspect of a respiratory valve according to the invention, at least a part of the valve housing is made from a transparent material for allowing visual observation of the valve flap.

According to yet a further aspect of a respiratory valve according to the invention, the valve flap is provided with a marking means to allow good visual observation of the valve flap, or a means for detecting a valve flap position.

According to yet a further aspect of a respiratory valve according to the invention, the means for allowing good visual observation is a coloration providing a contrast to a valve housing colour and a part of the valve housing is made from a transparent material.

A valve according to the present invention provides a number of advantages over prior art valves.

In particular, as the valve of the present invention generally is operated by the gas flow generated by manipulation of the bag in the assisted ventilation mode, and/or by the lung function of the patient in the spontaneous breathing mode, several advantageous qualities are provided.

One such quality is the advantage of avoiding a ventilation mode selector arrangement known from prior art valves, that in some designs require manual manipulation for the prior art valve to operate properly and/or in the desired ventilation mode. The avoidance of such a mode selector arrangement can contribute to reduce the stress on the operator, and can mitigate a possible risk to the patient as well as to the operator due to an incorrect operation of the mode selector.

Another such quality is the reduced risk of anaesthetic gas leakage that could affect the personnel located in the environment where the valve is being used. As previously noted, certain prior art valves do exhibit operational characteristics that may pose such a risk, in cases where the valve, under what should be considered normal operating conditions, enters a state of jamming, sticking or locking, at which point a bypass valve or relief valve is activated, or in the worst case where the gas conduits must be disconnected from the valve in order to bring the valve back to a normal operating state. By embodying the principles of the valve of the present invention into a properly designed valve, a valve according to the invention is realized that cannot be brought into a locked state under normal operating conditions. It should be understood, that normal operating conditions is to include rapid changes in flow or pressure, as well as rapid changes in flow and pressure at the same time, such as at a puff or a cough from the patient, or at an abrupt operation of the bag.

Yet a further quality relates to the simplicity of the design of a valve according to the present invention. The small number of individual parts allow for simple manufacturing, at a highly competitive price. By keeping the number of parts to a minimum, safe operation in the long term is guaranteed, without requiring extensive maintenance, adjustments and calibration.

According to yet a further quality, does the valve of the invention lend itself to be manufactured from a selection of materials that give the valve very long shelf life, still at a low cost. This is in contrast to a number of prior art valves that require, for example, flexible elements made from rubber like materials that typically may have limited shelf and operational lifetime or may be expensive, or such valves that employ moveable elements in conjunction with shafts or guides that require maintenance of properly lubricated interfaces between the moveable and stationary parts of the valve.

In a preferred embodiment is the aforementioned quality relating to simple construction and use of low cost materials with long shelf life employed in the manufacturing of a highly attractive disposable valve. A disposable valve exhibiting the advantageous characteristics of the valve of the invention will eliminate the need for repeated cleaning and sterilization, without burdening the budget. The disposable valve will ensure patient safety by eliminating the need for dismantling and reassembling operations. By elimination of such operations, the increased risk of equipment malfunctioning at a critical time known to be related to maintenance operations is eliminated, or at least significantly reduced.

A valve according to the present invention may be delivered as a sterile unit, whether it be as a disposable valve or as a re-usable valve.

The design of the valve of the invention lends itself to be manufactured from a transparent material, giving the advantage of allowing the operator at all times to observe the operation of the one moveable part of the valve. Thus, the state and condition of the valve can be determined fully without having to resort to any disassembly operations, whether it be at the manufacturing stage, while under storage, in a process of being cleaned and sterilized, or during its intended employment.

In the following, the invention will be explained by way of example, and by reference to the accompanying drawings, wherein;

FIGS. 1A and 1B are perspective views of a valve according to the invention,

FIGS. 2A, 2B, 2C and 2D are sectional drawings of an exemplary embodiment of a valve according to the invention indicating the operating principle, FIGS. 3A, 3B, 3C and 3D are sectional drawings of an exemplary embodiment of the present invention further explaining its principle of operation, FIG. 3E is a sectional view providing a detail of an embodiment of the present invention, FIGS. 4A and 4B are perspective and sectional drawings, respectively, of a further embodiment of a valve according to the invention, FIG. 5 is a sectional drawing of a further embodiment of an exemplary valve according to the invention, FIGS. 6A, 6B and 6C are sectional drawings of a further embodiment of an exemplary valve according to the invention for explaining its design and operating principle, and FIG. 7 is a sectional view of an exemplary embodiment of an anaesthetic apparatus including a valve according to the invention.

It should be noted that in the accompanying drawings for explanation of the valve of the present invention by way of example, the drawings are not intended to depict the valve to a particular scale. Accordingly, the various features of the valve of the invention may be varied, while maintaining the features providing the advantageous characteristics of the inventive valve. As non-limiting examples of such variations may be mentioned the length of the valve flap 30, the height, depth and width of the housing 10, the extension of the interior surface 17 towards the inlet opening 21, the location of the inlet opening 21 in relation to the upper or lower part of the housing 10, the location of the outlet opening 23 in the slanting or arcuated interior wall sections 18, 19, the point of coupling of the lower part 31 of the flap 30 to the housing 10, and so on.

Reference is first made to FIG. 1A. An exemplary valve 100 according to the invention, typically comprising a valve housing 10 having a lower section 13 in which lower section 13 a movable flap 30 is attached to the housing 10. The perspective view of FIG. 1A indicates the interior shape of the housing 10, in which an upper part of the flap 30 away from the lower part 13 is allowed to move between a substantially flat front wall 11 and a curved or tilted rear wall 14. An upper part 15 of the housing is recessed into the interior area of the housing 10, such that, as the flap 30 moves away from the front wall 11 towards the curved rear wall 14, said recessed upper part 15 of the housing is located immediately adjacent to an upper edge of the flap 30 for a substantial part of the free travel range for the upper part of the flap 30. By this, fluid communication through the valve may be allowed partly when the flap 30 is in an idle position, located adjacent to the front wall 11, essentially blocked when the flap 30 is positioned with the upper edge of the flap 30 adjacent to the recessed upper part 15 of the housing, and fully opened from the inlet opening 21 to a supply opening 22 when the flap 30 is located adjacent to the rear wall 14. A more detailed description of the operational aspects will be provided below.

With reference to FIG. 1B, it is shown that the valve is provided with an inlet opening 21, a patient side opening 22 and an outlet opening 23. The transversal dimension of the flap 30 is such that side edges 33, 34 remain immediately adjacent to the interior surface of side walls 12a, 12b, respectively, such that gas is not allowed to pass between the side edges 33, 34 and respective interior parts of the side walls 12a, 12b. As the side edges 33, 34, partly the upper edge 32, and the lower part 31 of the flap 30 is located inside the housing 10, these details are drawn in FIG. 1B with broken lines. As explained above, the lower part of the flap 30 is in the region of the lower edge 31 attached to the housing 10 in the area of the lower part 13 of the housing 10. The patient side opening 22 and outlet opening 23 are also drawn with broken lines to indicate that they are provided in the upper rear wall part 16 and lower rear wall part 14, respectively, which are not visible with the perspective view angle of the illustration of the valve 100 in FIGS. 1A and 1B.

Several variations of the outline of the valve housing 10 are contemplated, as the illustration provided by FIGS. 1A and 1B are drawn to reflect the shape of the interior space of the housing 10. Also, other shapes of the interior part of the housing 10 are contemplated, and some variants will be described in the following.

Now, reference is made to FIGS. 2A, 2B, 2C and 2D to explain the operation of a valve according to the invention.

Firstly, with reference to FIG. 2A, the valve is illustrated in a sectional view, in an idle position. In a preferred embodiment of the invention, provisions are made such that the flap 30, conveniently drawn in the illustration of FIG. 2A by way of a broken line such that it can be distinguished from parts of the housing 10, remains located adjacent to the inner surface 20 of the front wall 11, and to fully or partly cover the inlet opening 21 provided in the front wall 11. In this drawing, the interior surface 17 of the recessed, or inwards projecting, part 15 in the top part of the housing 10 is identified, as well as the curved interior surfaces 18, 19 of the rear wall forepart 14. The degree to which the inlet opening 21 is covered by the upper part of the flap 30 is given by the size and shape of the inlet opening 21, its positioning in the front wall 11 and the length of the flap 30. When gas is supplied to the inlet opening 21, the gas having a pressure or provided with a flow rate that is different from the pressure or flow rate, respectively, at the patient side opening 22, the gas pressure or gas flow will apply a force to the flexible flap 30, to produce a movement of the flap 30 away from the inlet opening 21. Depending on the shape of the front inner section 24 of the upper part of the interior of the housing 10, some degree of by-pass flow can be accommodated for controlling the input gas flow or gas pressure required to bend the flap away from the inlet opening and towards the front edge of the inner surface 17 of the recessed, or inwards projecting, part 15 of the upper part of the housing. Provided that there is sufficient flow and pressure to move the upper part of the flap 30 to the forward edge of the interior surface 17 of the recessed part 15 of the upper part of the housing 10, as shown in FIG. 2B, the upper edge 32 of the flap 30 will be located immediately adjacent to the inner surface 17, to block off the by-pass that is provided by the space between the upper edge 32 and the interior surface 24. Preferably, the inner surface 17 is essentially describing the path followed by the upper edge 32 of the flap 30 as it moves from the idle position, away from the inner surface 20 of the front wall 11, and towards the working position by the inner surfaces 18, 19 of the rear wall 14. Accordingly, the inner surface 17 should be appropriately curved to keep gas from leaking past the upper edge 32 and between the inlet side and respiration side of the housing as the valve flap moves past the inner surface 17, that is, as the upper edge 32 is positioned adjacent to the inner surface 17. In an alternative embodiment, the inner surface 17 may be provided with a different shape, if it is desirable obtain a different operational characteristic of the valve, such as for example by allowing gas to be communicated between the inlet side and the respiration side of the housing while the valve flap is positioned with its upper edge 32 adjacent to the inner surface 17. With a continued application of gas flow or gas pressure to the inlet opening 21, such as by continued operation of a bag connected to the inlet opening, the flap 30 will be forced, as shown in FIG. 2C, further away from the interior surface 20 of the front wall 11, and consequently move closer to the inner surfaces 19, 18 of the rear wall 14. Before the upper edge 32 reaches the rear edge of the inner surface 17, the lower part of the flap 30 will be located such that it substantially covers the outlet opening 23, thereby blocking gas supplied to the inlet opening from exiting through the outlet opening 23.

With reference to FIG. 2D, it is shown that with an adequate supply of gas through the inlet opening 21, the flap 30 has moved such that the upper edge 32 is positioned beyond the rear edge of the interior surface 17 of the upper part of the housing 10, such that the gas supplied through the inlet opening 21 is allowed to pass through the valve and to exit through the patient side opening 22. In an anaesthesia breathing apparatus, typically, a bag is connected to the inlet opening for assisting a patient that is not breathing spontaneously.

The gas flow or pressure required through the inlet opening to move the flap from the idle position shown in FIG. 2A, through the intermediate position shown in FIGS. 2B and 2C, and to the working position shown in FIG. 2D can be controlled by adjusting the material from which the flap 32 is made, its length, thickness, width and point of fixation to the housing 10, or any combination of the aforementioned.

It should be noted that, although the valve of the invention is explained herein by way of a preferred embodiment with the flap itself serving as the means to close the outlet opening when the flap is in the working position, the closing means could be provided by a closing valve means (not shown in the drawings) located in conjunction with the outlet opening and being made operationally associated with, or acted on by, the flap so as to close the communication between the interior of the valve housing and the outlet opening when the flap becomes positioned in or at the working position.

It should be noted that the design details regarding the arcuated or slanted interior wall sections 18, 19, together with the shape and size of the flap and the interior shape and size of the upper part of the housing 10, are selected such that in case of an abrupt increase in a gas flow into the respiration opening, such as due to a cough from a patient who is connected to the respiration opening, the flap will not remain forced, or "locked", against the part of the interior wall sections where the outlet opening is located. In particular, it has been found that by making an arcuated part of the interior wall sections 18, 19, i.e. the sections extending between the bottom of the housing and a location above the outlet opening, with a large radius of curvature and the remaining part above with a smaller radius of curvature, locking can be eliminated. As an alternative to a smooth transition from a large radius of curvature to smaller radius of curvature for the remaining, upper part of the interior wall sections 18, 19, as indicated in the drawings, a bend may be introduced in the upper section 18 between a lower part with a large radius of curvature and an upper part that may be arcuated or slanting in a direction away from the opposite interior wall 20. Thereby, if an abrupt increase in flow or pressure occurs from the respiration opening, a torque may be produced by the flap at the point where the flap encounters the bend "transition". The torque thus produced will, with the flap and its surroundings properly designed, lift a lower part of the flap from the outlet opening to allow a gas flow to the outlet opening in order to provide relief through the outlet opening for the sudden pressure increase.

Correspondingly, by properly designing the extension of the flap into the upper part of the housing, and the dimensions and location of the upper interior wall section 17, the flap will be properly driven away from the interior wall sections 18, 19 to create a passage between the respiration opening and the outlet opening, also in the case of a strong and abrupt increase in the pressure or flow of gas coming into the respiration opening.

The inlet opening may be located on the inlet side of the housing differently from what is shown in the illustrative examples provided in the accompanying drawings. As an example, the inlet opening may be located further down on the inlet side wall 11, and still provide a valve according to the invention. A location different from what has been illustrated in the drawings may be advantageous, such as for the control of the movement of the flap in either direction, or the control of a "return flow" of gas entering the inlet opening from the housing, that is advantageous for bag filling.

The passage provided to allow for a "return flow" of gas from the housing to the inlet opening may be arranged by other means than the passage illustrated in the drawings, a gap obtained by terminating the upper part of the flap below an upper edge of the inlet opening. Several alternatives are contemplated, such as providing a similar gap or opening on the side of the flap instead of at the top, or by providing a separate passageway on the inlet side opening between the interior of the housing and the inlet opening, or between the patient side opening area and the inlet opening.

Now, reference is made to FIGS. 3A, 3B, 3C and 3D for explaining the operation of the valve when changing its operational mode from a mode wherein gas is supplied to the patient to a mode where gas exhaled from the patient is allowed to flow from the patient side opening 22 to the outlet opening 23, preferably also providing a controlled gas by-pass to provide a certain amount of gas to exit through the inlet opening 21 for the purpose of filling a bag connected to the inlet opening 21.

Assuming that the valve is in the operational position illustrated in FIG. 2D, a gas supply is provided to the patient side opening 22. Depending on the properties of the flap 30, only a slight pressure or flow of gas supplied to the patient side opening may be required to operate the valve, or, provided that the flap 30 has resilient properties or is provided with some means for returning the flap to the idle position, the valve may not require any gas supply provided through the patient side opening 22 for returning the flap to the idle position. However, for the purpose of explaining the invention, it is now assumed that the resilient properties of the flap are such that it will not immediately return to the idle position, but that sufficient resilience is provided for the flap to move slightly away from the upper part of the inner surface 18 of the rear wall 14, such that it can be impacted by the gas flow input through the patient side opening to drive the flap away from the upper part of the inner surface 18 and towards the front edge of the inner surface 17 of the upper part 15 of the housing 10. By the gas flow or pressure provided by input through the patient side opening 22, the flap 30 is driven away from the rear wall 14, and at some point the lower part of the flap 30 will have moved away sufficiently to allow gas to flow from the patient side opening to the outlet opening 23. By continuous provision of gas through the inlet opening 22, such as by the exhalation provided by the lunges of a patient connected to the patient side opening 22, the flap 30, as shown in FIG. 3C, will continually be forced away from the interior surfaces 18, 19 of the rear wall 14, and towards the interior surface 20 of the front wall 11. The movement of the flap 30 away from the inner surfaces 18, 19 will provide a passage to be created between the patient side opening 22 and the outlet opening 23, and eventually, as shown in FIG. 3D, a passage having dimensions that provide substantially free flow of gas from the patient side opening to the outlet opening. Eventually, shown in FIG. 3D, the flap 30 will have moved back to the idle position, whereby full exhalation from the patient is allowed through the outlet opening 23, and, depending on the interior shape of the interior part 24 of the upper part of the housing 10, the size, shape and location of the inlet opening 21 in the front wall 11 and its relation to the upper edge 32 of the flap, a certain by-pass flow is provided for refilling a bag that is connected to the inlet opening 21.

In an alternative and advantageous embodiment of the valve of the invention, the wall sections 18, 19 exhibit a specific feature, generally illustrated by an example in the enlarged sectional view of FIG. 3E. The illustration in FIG. 3E is limited to show the section of the patient side wall 14 of the housing, sections of parts of the side walls 12a and 12b, and including broken lines to illustrate the position of the outlet opening actually situated at a point below the point of sectioning. The section is taken along the line A-A shown in FIG. 3D. A passageway 70, such as a channel or slot 70 in the wall sections 18, 19, is provided to allow gas to be communicated from the area of the patient side opening into a part of the housing interior being situated below the patient side opening and on the patient side of the flap. For symmetry, two passageways may be provided, as illustrated in FIG. 3E. Thus, when having gone from inhalation to exhalation, not only the part of the flap close to the patient side opening will be acted on by gas entering the valve from the patient side opening, but gas provided by the passageway will act on other parts of the flap where gas in the passageway or channel gets into contact with the flap, to further facilitate movement of the flap away from the wall sections 18, 19.

Having explained the operation of a valve according to the invention, and its operation through the breath-in through breath-out cycle when used with a bag connected to the inlet opening and the lunges of a patient connected to the patient side opening, in the following, further advantageous embodiments of the valve of the invention will be explained.

Reference is now made to FIGS. 4A and 4B, illustrating in the perspective view of FIG. 4A, and a cross section view in FIG. 4B, wherein, as in the previous drawings, the flap is illustrated by a broken line, the valve has been equipped with adapters 41, 42 and 43, the adapters being dimensioned to the typical sizes of conduits used for connecting, by way of the inlet side adapter 41 to a bag, by way of the patient side adapter 42 to a conduit for connection to a patient mouth piece or mask, and the adapter 43 for connecting to an outlet conduit to be used for transporting gas away from the apparatus.

Reference is now made to FIG. 5, showing a further exemplary embodiment of a valve according to the invention. In the embodiment shown in FIG. 5, the upper part of the housing has a different shape from what is shown in the previous figures, whereby the inner surface 17 has been extended all away to the inlet opening, the shape of which interior surface 17 is adapted to closely follow the trajectory path followed by the upper edge 32 of the flap as it moves from the idle position to the fully operational position. The embodiment illustrated in FIG. 5 is also provided with a gas surplus check valve 60, such that a potential high pressure within the valve can be released to avoid over-pressuring the lunges of a patient connected to the patient side opening of the valve. Several alternative surplus check valves may be employed with the valve of the invention. The surplus valve 60 example shown in FIG. 5 comprises a valve seat 61, a valve sealing disc 62 and a bias spring 63, together with a tensioning arrangement 64. The sealing disc 62 is forced against the seat 61 by the bias spring 63, the force of which biasing spring is controlled by the tensioning arrangement 64. If a force applied to the sealing disc 62 by internal pressure in the housing 10, exceeds the sum of the force applied from gas pressure outside the housing and the force applied by the biasing spring, the sealing disc will be lifted away from the seat and allow gas to exit from the housing 10 through the surplus valve. The pressure at which the surplus valve be activated can be set by operating the tensioning arrangement that in turn controls the tensioning of the biasing spring, and hence the force applied to the sealing disc to hold it against the seat.

The embodiment shown in FIG. 5 also includes a PEEP (Positive End Expiratory Pressure) valve 50, to ensure that a minimum breathing gas pressure is maintained. The inclusion of a PEEP valve 50 is particularly desirable to provide a flow of breathing gas into a bag connected to the input opening, thereby ensuring filling of the bag with breathing gas. The PEEP valve 50 illustrated in FIG. 5 comprises a housing 51, a valve seat 52 and a valve flap 53, the latter of which has been shown with a broken line to indicate that the flap 53 is flexible or movable to allow the flap 53 to remain against the valve seat 52 in an idle position or when an attempt is made to establish a return flow of gas input through the outlet opening 23, and to allow a gas flow exiting through the outlet opening 23 to flow substantially freely or at a resistance or pressure set by the PEEP valve. The inclusion of a PEEP valve 50 is particularly desirable when a conduit is applied for transporting gas away from the outlet opening 23, such that a spontaneously breathing patient will not re-inhale gas that previously has been exhaled through the valve 100, and such that the proper positive pressure can be established and maintained in the patient system. The embodiment of FIG. 5 exhibits an inner surface 17 in the uppermost part of the housing extended substantially all the way to the inlet opening, or close to where the upper edge of the flap is located when situated in the idle position. The shaping of the inner surface in the vicinity of the inlet opening should be shaped appropriately so as to allow gas to flow back to the inlet opening if filling of a bag from gas in the valve housing is required.

Now, reference is made to FIGS. 6A, 6B and 6C, which figures have been included to illustrate, by way of a further embodiment, that the valve may be given a different exterior shape than what has been shown in the previous drawings, while still providing an interior shape and provisionings for flap, slanted or arcuated interior wall sections, housing upper part inner surface and corresponding openings and other internal features to provide a valve exhibiting the features of the invention. In FIG. 6A, this embodiment of the valve of the invention is in an idle position, in FIG. 6B is in a fully operational position allowing gas to flow from an inlet opening through to a patient side opening, and, in FIG. 6C, in an exhalation state allowing gas exhaled by a patient connected to the patient side opening to flow through the valve to an outlet opening. For filling of a bag coupled to the inlet opening, provisions should be made for a partial flow back through the inlet opening.

In the following, certain aspects relating to the valve of the present invention will be explained.

Reference is first made to FIGS. 2A, 2B, 2C and 2D.

In FIGS. 2A through 2D is shown an embodiment of the invention, wherein the flap 30 is a sheet of a flexible material capable of maintaining an overall rectangular shape fit to certain internal rectangular shape and dimensions of the exemplary housing 10, and being attached to the housing 10 in a lower part 13 (bottom) at its lower edge 31. By selecting an appropriate material for the flap, for example a type of flexible plastic material, resilience of the flap 30 can be obtained such that the flap, after having been moved away from the front wall 11, automatically will return to its idle position as shown in FIG. 2A. However, the flap may also be attached and positioned within the housing, depending on its operational characteristics and operational use, such that, in the idle position, the upper edge 32 of the flap is located immediately adjacent to the inner surface 17 of the upper part of the housing 10, almost as illustrated in FIG. 2B, such that a certain gas flow or gas pressure is required for moving the flap 30 to either side. Furthermore, the flap need not have a rectangular shape as shown in the exemplary embodiments of the accompanying figures. The housing may be provided with varying internal dimensions, with the flap dimensioned accordingly to provide the necessary sealing along its side edges to avoid gas from flowing or leaking past the flap, when such sealing is required.

The embodiments of the valve illustrated herein, show that the interior surfaces 18, 19 of the rear wall 14 are curved, and the radius of curvature of the surfaces is progressively reduced in the upper part of the housing. However, the inner surfaces 18, 19 can be represented by straight line surfaces, and be adapted to the properties of a flap made from different materials and having different dimensions depending on the desired operational modes and characteristics of the valve. Furthermore, the flap need not be flexible or resilient in its entire length. As an example, a lower part of the flap could be a rigid plate element hinged to the housing, that, when moved close to the interior surfaces 18, 19 of the rear wall 14 fits over the outlet opening 23. With a corresponding modification of the interior surface 17 of the upper part of the housing 10, a flow of gas would be allowed between the inlet opening 21 and the patient side opening 22 when the upper edge of the flap 30 passes the rear edge of the inner surface 17 at a point which is different from the embodiments that have been illustrated in the accompanying drawings. It is also contemplated that, by providing a biasing arrangement at some point along the flap 30, the operational characteristics of the valve of the invention can be made controllable, such as for example by applying a spring with a tensioning arrangement, or by employing some sort of movable retaining device made movable in the longitudinal direction of the flap 30 illustrated in FIGS. 2A-2D, to modify the point at which the flap is attached to the housing.

In an advantageous embodiment of a valve according to the invention, the housing 10 is made from a transparent material which fully or in part allows an observation of the position of the flap, such that the dynamic operation of the valve can be observed, for example for determining proper operation of the valve. For visual observation, the flap should preferably be provided with a colour that facilitates observation of the flap and its positioning or movement within the housing. Possibly, only the side walls 12a or 12b can be made from a transparent material, or, as an alternative, any part of the housing 10 can be made transparent to the extent that the transparent part allows observation of the flap 30 inside the housing 10.

For unmanned observation of the valve, the valve can advantageously be provided with a detection device to detect the movement of the flap 30 inside the housing, or, to detect the flap 30 in different positions, in order to determine proper operation of the valve, or/and determine the setting of a valve provided with a means for controlling its operational modes, as explained earlier.

In yet another embodiment of the valve, the recessed part of the interior of the housing, which, in the illustrated embodiments of the invention are designated by numerals 15, 17 and 24, can be provided in a side wall, such as side walls 12a or 12b, rather than in the top wall 15 to provide the various operational modes and positions explained herein.

In a preferred embodiment of the valve of the invention, is the valve furnished with markings that clearly show where and how to connect different conduits to the various inlets and outlets. As an alternative or a supplement to the aforementioned markings, the valve according to the invention can be provided with connectors of different types or having keying features for use with conduits equipped with corresponding type connectors, depending on whether the connection is for a bag, for a gas conduit leading to the patient, or a conduit for leading used gas or surplus gas away from the scene of usage of the valve.

It should be noted that, in contrast to some prior art valves, a valve according to the present invention may generally be operated in any position. This means that, compared to the position used in the accompanying drawings for explaining the invention, the valve may just as well be operated when positioned upside down from the position shown in the attached drawings to explain the invention, as well as in any other position.

With reference to FIG. 7, an exemplary embodiment of an anaesthetic apparatus including a valve 100 according to the invention will be explained. A fresh gas input conduit 200 is provided, for delivering fresh gas to a patient via a mask 300. The mask 300 may be designed to fit over mouth and nose as appropriate to ensure that gas does not escape the coupling of the mask to the patient. Gas being exhaled from the patient or as surplus gas entering through the input conduit 200 is allowed to flow via the patient side conduit 400 to the valve 100. During exhalation, or between inhalation and exhalation, the flap is in the idle position providing a passage on the upper side of the flap that allows gas to flow through the bag conduit 500 and into the bag 600. The PEEP valve arranged at the output where the output conduit 700 is connected to the valve 100 ensures to maintain a positive pressure in the apparatus. After filling of the bag by gas having entered the valve from the patient side, the operator may squeeze the bag to drive gas back through the valve, thereby bringing the flap into the working position where it blocks the output and allowing the gas to flow back into the patient for assisted inhalation with a pressure controlled by the operation of the bag. Having provided gas by squeezing the bag for an appropriate period of time and with the appropriate force, the operator relaxes the squeezing force, which brings the flap back to the idle position, allowing the patient to exhale through the valve and exhaled gas to flow through the outlet conduit, and allowing part of the gas flowing into the valve to fill up the bag.

The invention claimed is:

1. Respiratory valve, comprising a valve housing with a chamber, the chamber having an inlet opening and a respiration opening arranged on respective inlet and respiration sides of said chamber, wherein the chamber is limited by an arcuated or aslant interior wall section extending from a lower part of said chamber and into an upper part of said chamber, which interior wall section is terminated in said upper part of said chamber and under the respiration opening, and that the respiratory valve further comprises an outlet opening, said outlet opening having an outlet opening width, said outlet opening being arranged in said interior wall section, and an elongated pliable or movable flap element in the form of a plate element in the form of a plate that extends in a direction of depth of said housing having a lower part connected to said lower part of said chamber, under the outlet opening, which plate element at the outlet opening is sufficiently wide to cover the outlet opening, and being terminated in an upper part of said interior chamber, which plate element is adapted to be positioned, in a rest position, in a distance from said interior wall section, and, in a work position, proximal to a part of said interior wall section, for in the work position substantially to cover and close the outlet opening and to establish a passageway between the respiration opening and inlet opening.

2. Respiratory valve according to claim 1, wherein said inlet opening and said respiration opening are arranged on respective inlet and respiration sides, of said housing situated on opposite sides of the valve flap.

3. Respiratory valve according to claim 1, wherein the plate element is adapted to be resilient or is provided with a return spring arrangement for positioning the plate element in the rest position.

4. Respiratory valve according to claim 1, wherein the valve housing comprises a top wall or a side wall having a part constituting a projection into the upper part of said interior space, which projection does not constitute an obstacle for a movement of the plate element, and which projection extends in a direction of depth of said housing from proximal to the inlet side wall and to a distance from the inlet side wall, which extent approximately corresponds to a distance between said inlet side wall and a point of said termination of said interior wall section in the upper part of said chamber.

5. Respiratory valve according to claim 1, comprising at least one of an inlet conduit arranged at the inlet opening, a respiration conduit arranged at the respiration opening and an outlet conduit arranged at the outlet opening.

6. Respiratory valve according to claim 1, comprising a PEEP valve arranged in communication with the outlet opening.

7. Respiratory valve according to claim 1, wherein said outlet opening is arranged in a central or lower part of said interior wall section.

8. Respiratory valve according to claim 1, wherein at least a part of the valve housing is made from a transparent material for allowing visual observation of the valve flap.

9. Respiratory valve according to claim 1, wherein the valve flap is provided with a marking means to allow visual observation of the valve flap, or a means for detecting a valve flap position.

10. Respiratory valve according to claim 9, wherein the means for allowing visual observation is a coloration providing a contrast to a valve housing colour and a part of the valve housing is made from a transparent material.

* * * * *